(12) United States Patent
Levy

(10) Patent No.: US 9,918,539 B2
(45) Date of Patent: Mar. 20, 2018

(54) HAND HELD DERMAPLANING DEVICE AND DERMAPLANING PROCESS

(71) Applicant: DD Karma LLC, Highland Park, IL (US)

(72) Inventor: Dara Levy, Highland Park, IL (US)

(73) Assignee: DD Karma LLC, Highland Park, IL (US)

( * ) Notice: Subject to any disclaimer, the term of this patent is extended or adjusted under 35 U.S.C. 154(b) by 0 days.

(21) Appl. No.: 14/062,262

(22) Filed: Oct. 24, 2013

(65) Prior Publication Data

US 2015/0073438 A1    Mar. 12, 2015

Related U.S. Application Data

(63) Continuation of application No. PCT/US2013/058708, filed on Sep. 9, 2013.

(51) Int. Cl.
| *A45D 44/22* | (2006.01) |
| *A61H 23/02* | (2006.01) |
| *A61H 7/00* | (2006.01) |

(52) U.S. Cl.
CPC ...... *A45D 44/22* (2013.01); *A45D 2200/1054* (2013.01); *A45D 2200/207* (2013.01); *A61H 7/005* (2013.01); *A61H 23/0245* (2013.01); *A61H 23/0263* (2013.01); *A61H 2201/1685* (2013.01); *A61H 2201/5005* (2013.01)

(58) Field of Classification Search
CPC .... A61H 23/0245; A61D 27/38; A45D 44/22; A61B 17/320068; A61B 17/320072; A61B 17/320076

USPC .............. 606/131, 133, 132, 169; 30/40.39
See application file for complete search history.

(56) References Cited

U.S. PATENT DOCUMENTS

| 917,043 A | 4/1909 | Gage |
| 1,139,796 A | 4/1914 | Parker |
| 3,509,626 A | 5/1970 | Mead |

(Continued)

FOREIGN PATENT DOCUMENTS

| DE | 9312913 | 10/1993 |
| EP | 0387176 | 9/1990 |

(Continued)

OTHER PUBLICATIONS http:/www.youtube.com/watch?v=W1PcSf253cs.

(Continued)

*Primary Examiner* — Anh Dang
(74) *Attorney, Agent, or Firm* — Wolf, Greenfield & Sacks, P.C.

(57) ABSTRACT

A method and a hand-held device for dermaplaning is disclosed that includes a blade with a safety cage forming an assembly removably mounted to a housing. The dermaplaning device is configured to limit the depth that the blade can penetrate the skin which makes the device safe for use by non-professionals. The dermaplaning device is electrically powered to cause the blade to vibrate at a predetermined frequency. Various embodiments of the hand-held dermaplaning device are disclosed for vibrating the blade. In accordance with an important aspect of the invention, the blade includes a safety guard for limiting the amount of penetration of the blade into the facial skin to enable the device to be safely used by non-professionals.

14 Claims, 16 Drawing Sheets

(56) References Cited

U.S. PATENT DOCUMENTS

| | | | |
|---|---|---|---|
| 3,636,627 A | 1/1972 | Tiffin | |
| 3,650,029 A | 3/1972 | Trelc | |
| 3,749,092 A | 7/1973 | Williams | |
| 3,967,143 A | 6/1976 | Watanabe et al. | |
| 4,146,958 A | 4/1979 | Chen et al. | |
| 4,335,508 A | 6/1982 | Francis et al. | |
| 4,709,476 A | 12/1987 | Shurtleff et al. | |
| 4,739,553 A | 4/1988 | Lazarchik | |
| 4,928,716 A | 5/1990 | Greene | |
| 5,016,352 A | 5/1991 | Metcalf | |
| 5,026,387 A * | 6/1991 | Thomas | 606/169 |
| 5,095,619 A | 3/1992 | Davis et al. | |
| 5,113,585 A | 5/1992 | Rogers et al. | |
| 5,191,712 A | 3/1993 | Crook et al. | |
| 5,207,696 A * | 5/1993 | Matwijcow | 606/167 |
| 5,220,728 A | 6/1993 | Ueno et al. | |
| 5,249,361 A | 10/1993 | Apprille, Jr. et al. | |
| 5,299,354 A | 4/1994 | Metcalf et al. | |
| 5,324,299 A * | 6/1994 | Davison et al. | 606/167 |
| 5,410,810 A | 5/1995 | Gillibrand | |
| D361,866 S | 8/1995 | Febus | |
| 5,518,114 A | 5/1996 | Kohring et al. | |
| 5,702,351 A | 12/1997 | Bar-Or et al. | |
| 5,931,859 A | 8/1999 | Burke | |
| 5,934,291 A | 8/1999 | Andrews | |
| 6,119,035 A | 9/2000 | Wang | |
| 6,119,038 A | 9/2000 | Cook | |
| 6,164,290 A | 12/2000 | Andrews | |
| 6,224,565 B1 * | 5/2001 | Cimino | A61B 17/32006 604/163 |
| 6,629,983 B1 | 10/2003 | Ignon | |
| D531,754 S | 11/2006 | Lee | |
| D532,157 S | 11/2006 | Lee | |
| 7,384,405 B2 | 6/2008 | Rhodes | |
| 7,761,998 B2 | 7/2010 | Blaustein et al. | |
| 8,052,662 B2 | 11/2011 | Zelickson et al. | |
| 8,132,332 B2 * | 3/2012 | Tautscher et al. | 30/43.92 |
| 8,745,876 B2 | 6/2014 | Hage et al. | |
| 2003/0233085 A1 | 12/2003 | Giammarusti | |
| 2004/0185067 A1 | 9/2004 | Daikuzono | |
| 2005/0043653 A1 | 2/2005 | Trimmer et al. | |
| 2005/0234477 A1 | 10/2005 | Brown et al. | |
| 2006/0032053 A1 | 2/2006 | Saker et al. | |
| 2006/0122631 A1 * | 6/2006 | Kertz | A61B 17/54 606/131 |
| 2006/0143926 A1 | 7/2006 | Khubani et al. | |
| 2007/0293795 A1 | 12/2007 | Carroll | |
| 2008/0139974 A1 | 6/2008 | Da Silva | |
| 2009/0048557 A1 | 2/2009 | Yeshunm et al. | |
| 2009/0124985 A1 | 5/2009 | Hasenoehrl et al. | |
| 2009/0235529 A1 | 9/2009 | Ringart et al. | |
| 2009/0270684 A1 | 10/2009 | Nielsen et al. | |
| 2009/0275864 A1 | 11/2009 | Hirai | |
| 2010/0168741 A1 * | 7/2010 | Sanai et al. | 606/42 |
| 2010/0228182 A1 | 9/2010 | Clark, III et al. | |
| 2010/0299928 A1 | 12/2010 | Clarke et al. | |
| 2012/0101512 A1 | 4/2012 | Locke et al. | |
| 2013/0073001 A1 | 3/2013 | Cambell | |
| 2013/0144280 A1 | 6/2013 | Eckhouse et al. | |
| 2016/0166273 A1 | 6/2016 | Levy | |
| 2017/0042568 A1 | 2/2017 | Levy | |
| 2017/0265629 A1 | 9/2017 | Levy | |

FOREIGN PATENT DOCUMENTS

| | | |
|---|---|---|
| EP | 0 451 381 | 10/1991 |
| EP | 1 972 417 | 9/2008 |
| EP | 1972417 | 9/2008 |
| FR | 2811524 | 1/2002 |
| GB | 2 398 533 | 2/2003 |
| GB | 2398533 | 8/2004 |
| JP | 2000060927 | 2/2000 |
| JP | 20000060427 | 2/2000 |
| JP | 2001245400 | 9/2001 |
| JP | 2003103074 | 4/2003 |
| JP | 2005270120 | 10/2005 |
| JP | 2009279293 | 12/2009 |
| KR | 20040022550 | 3/2004 |
| KR | 20080006875 | 1/2008 |
| RU | 2320476 | 3/2008 |
| WO | 2005002386 | 1/2005 |

OTHER PUBLICATIONS http://www.youtube.com/watch?NR=l&v=jypKlrpGDlg&feature=fvwp.
http://www.youtubecom/watch?v=fmSS2uexmac.
http://dermasonic.com/how.html.
U.S. Appl. No. 15/585,840, filed May 3, 2017, Levy.
U.S. Appl. No. 14/976,409, filed Dec. 21, 2015, Levy.
U.S. Appl. No. 14/742,881, filed Jun. 18, 2015, Levy.

* cited by examiner

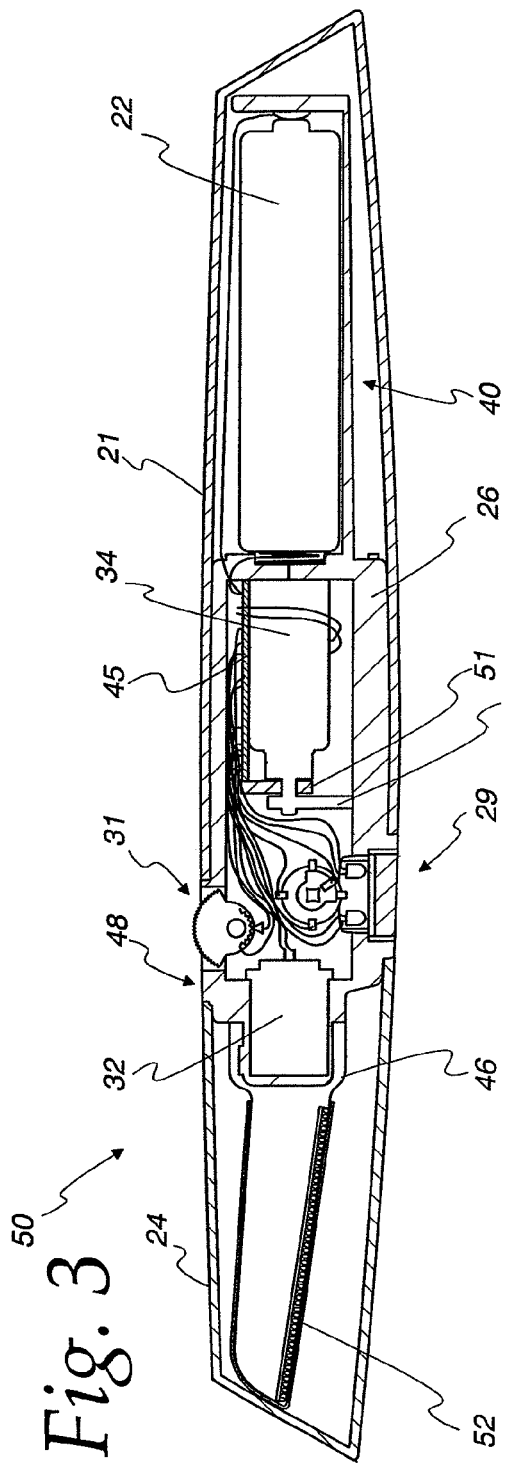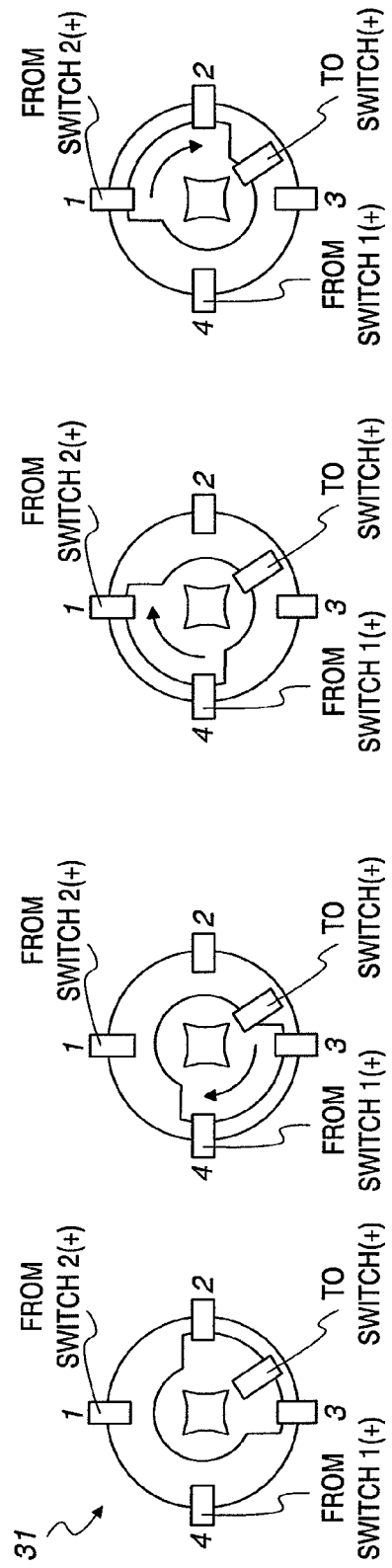

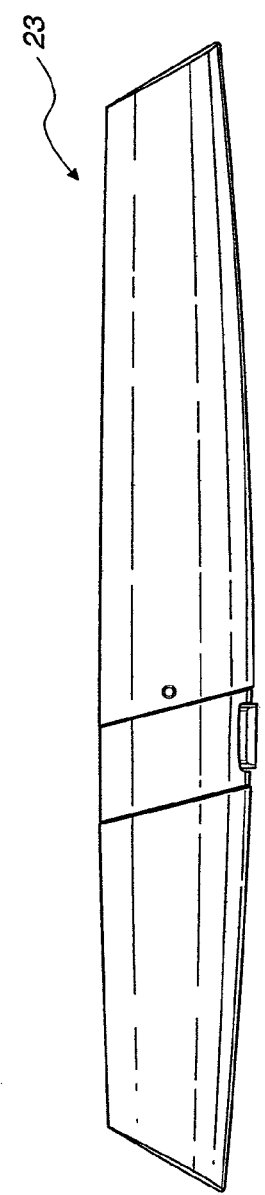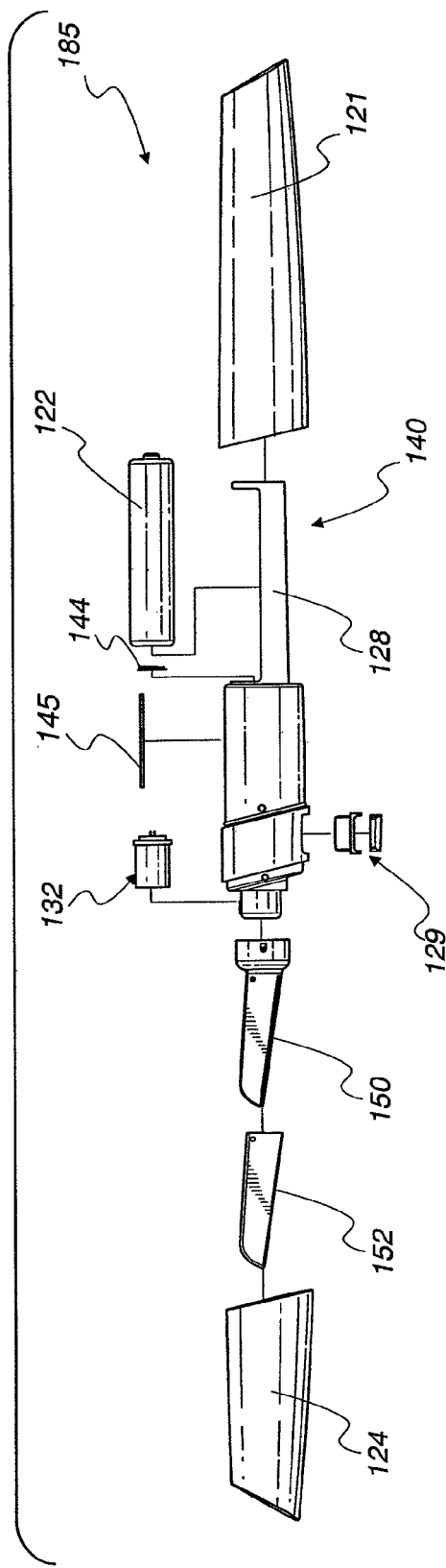
Fig. 7
Fig. 8

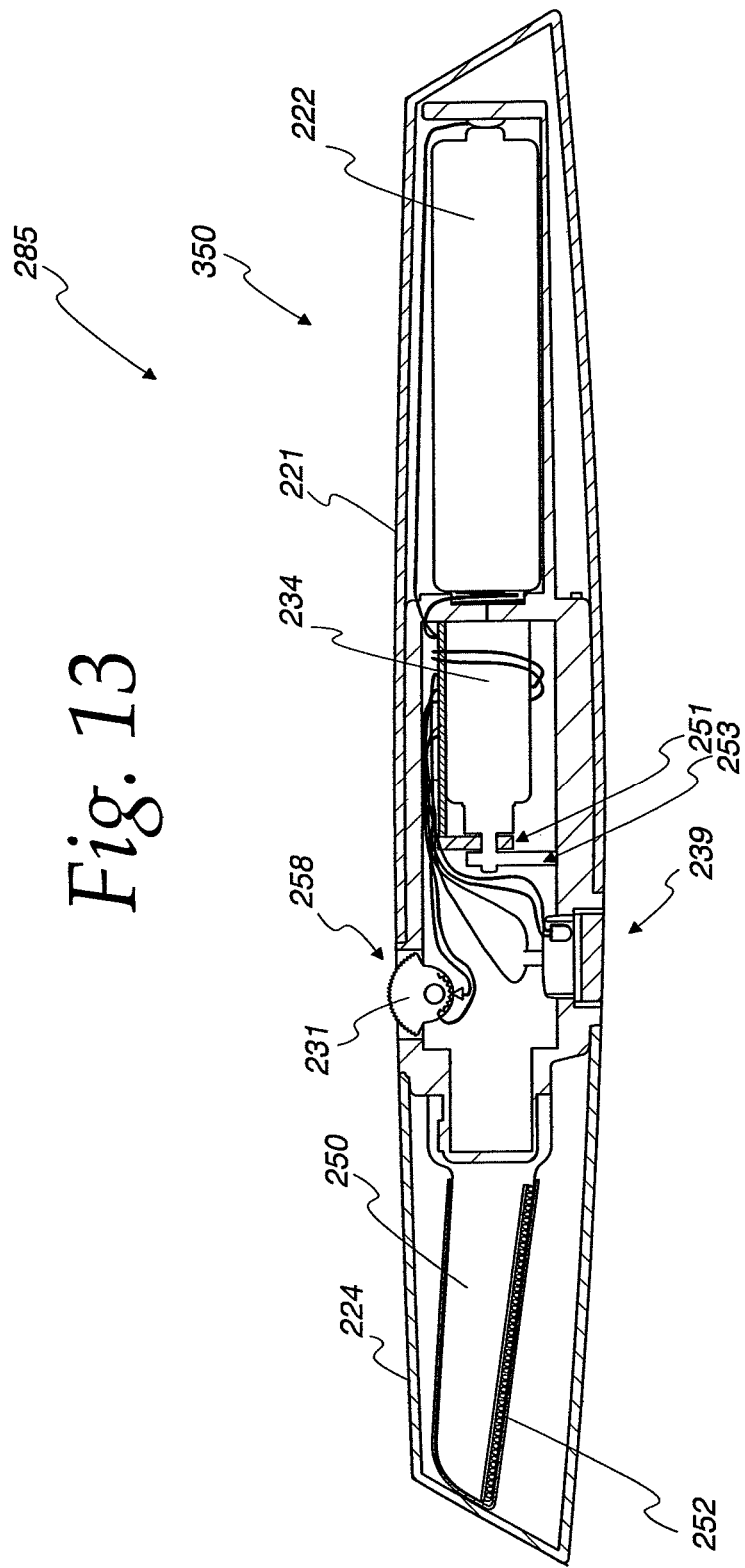

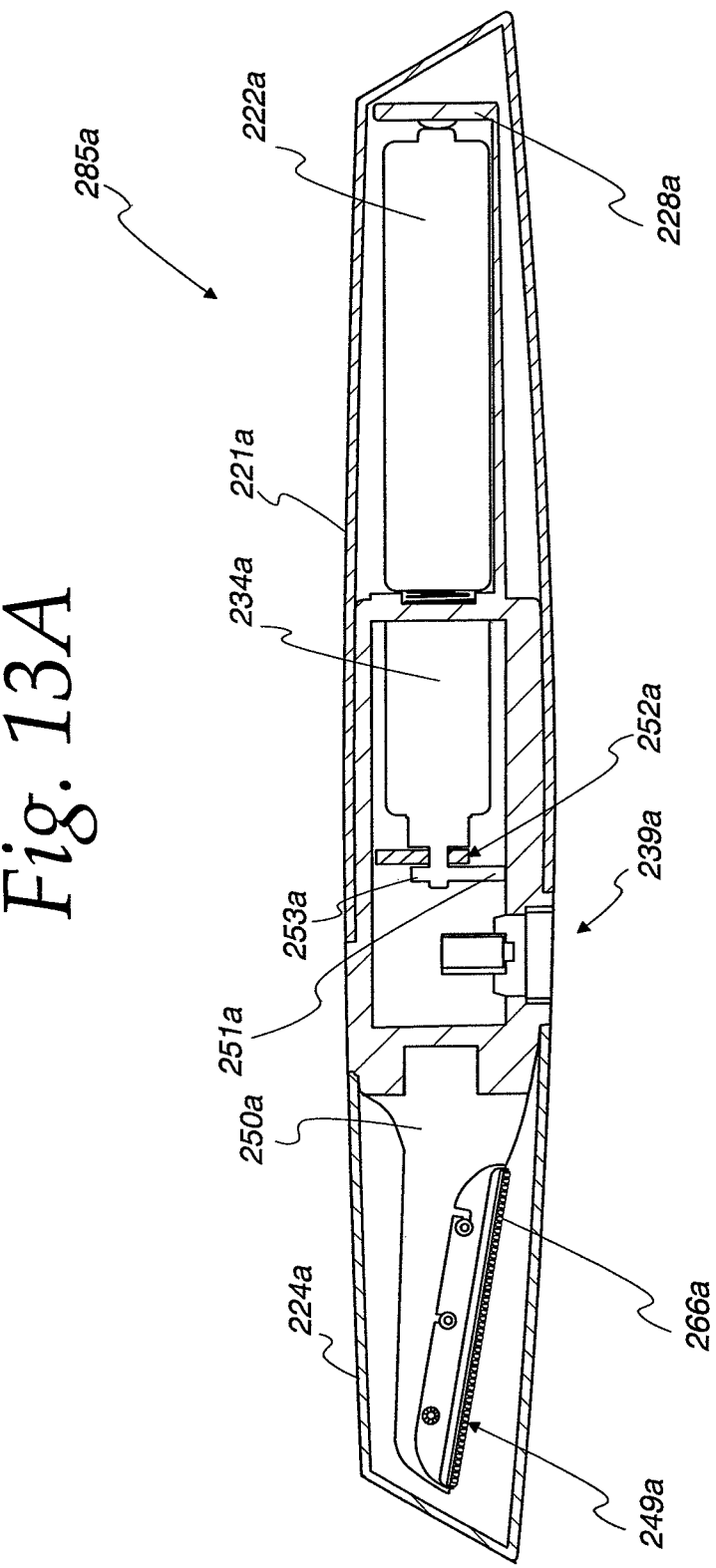

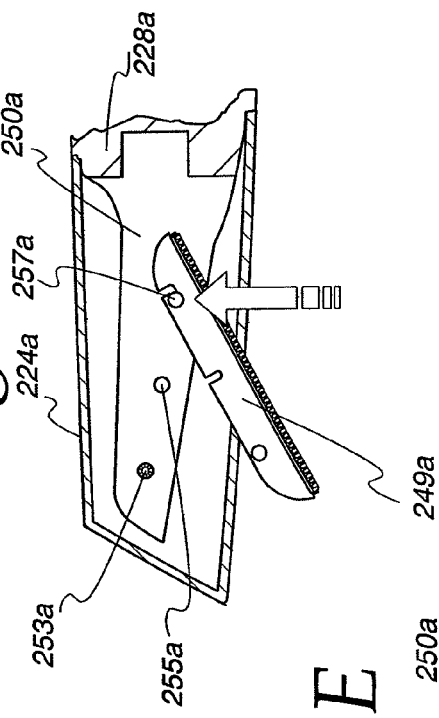
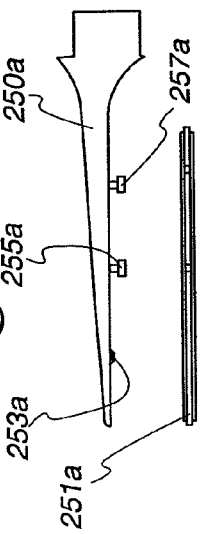
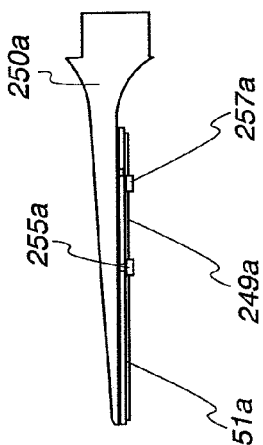
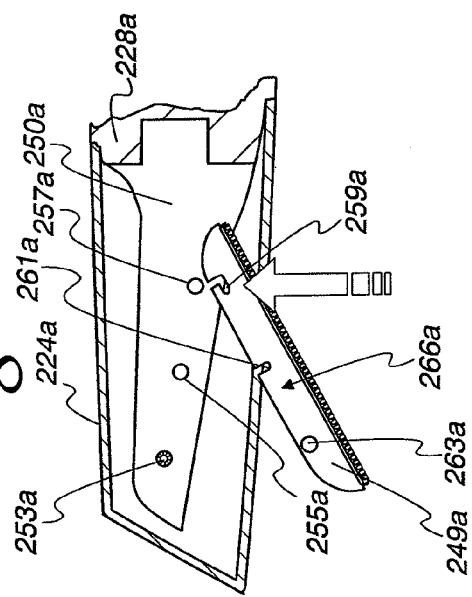
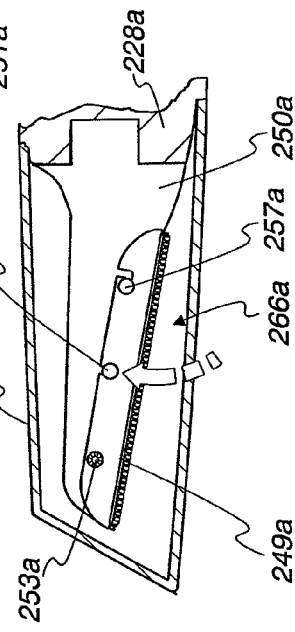

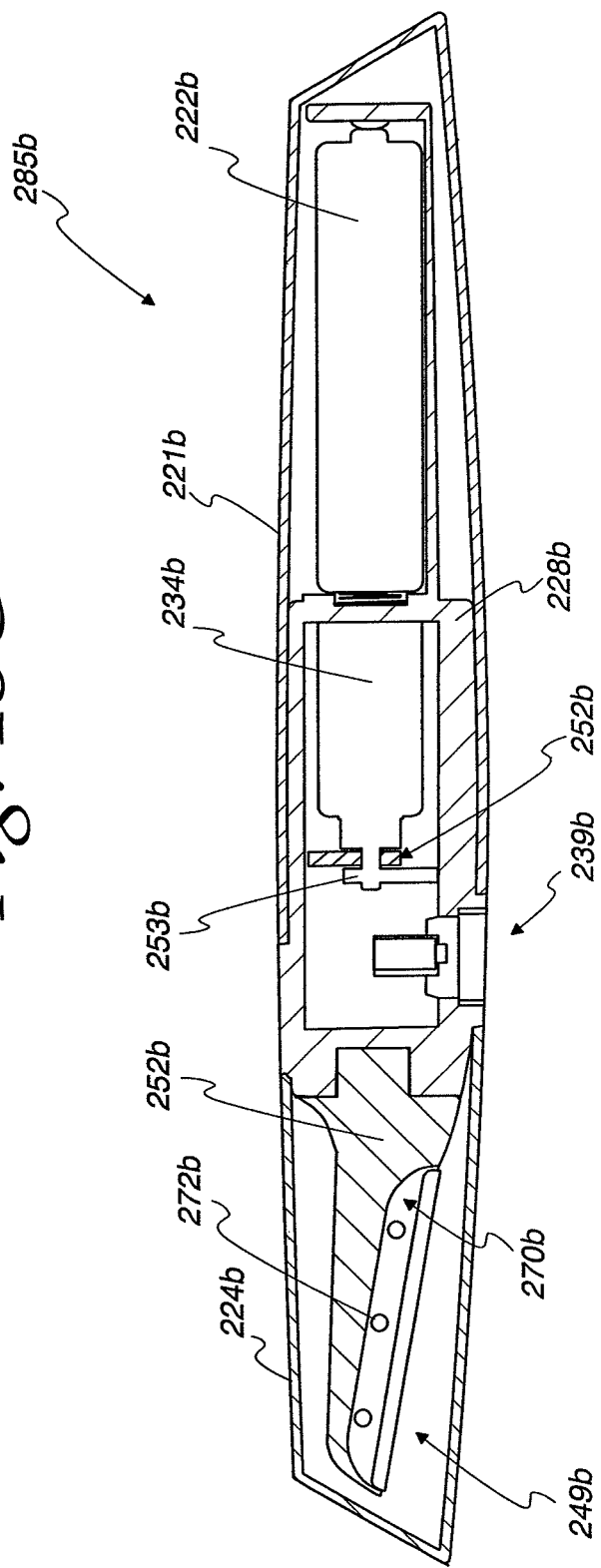

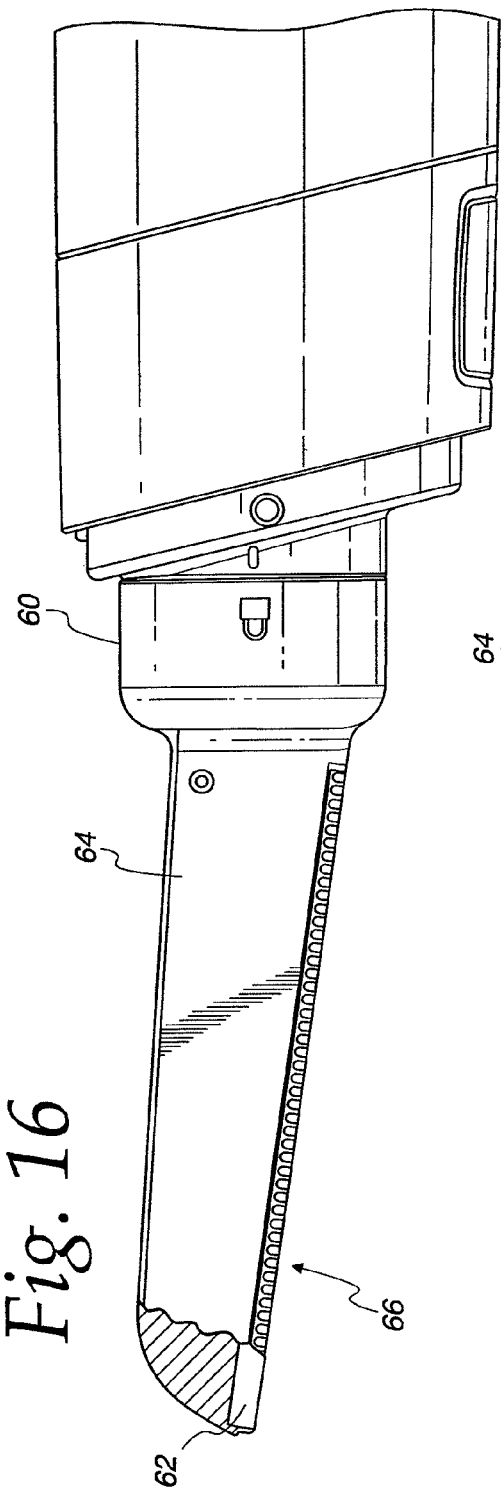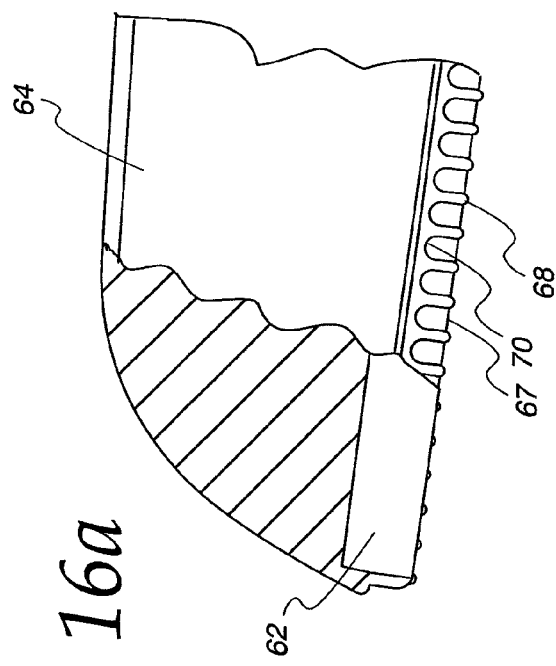

HAND HELD DERMAPLANING DEVICE AND DERMAPLANING PROCESS

BACKGROUND OF THE INVENTION

1. Field of the Invention

The present invention relates to hand held device and process used in treating facial skin and more particularly to a hand held dermaplaning device for exfoliating facial skin that is safe to use by non-professionals as well as a process for dermaplaning facial skin.

2. Description of the Prior Art

Various processes are known for treating facial skin. These processes are known to include hand-held devices and fall into several categories as follows:

Shaving
Cleansing and Moisturizing
Dermabrasion
Dermaplaning (Exfoliation)
Debridement Shaving is used to remove facial hair by way of a razor. In addition to standard safety razors, U.S. Pat. No. 3,509,626 and Russian Patent RU 2320476 disclose safety razors with piezo-electric crystals attached to the blade for vibrating the blade at ultrasonic frequencies during shaving. These devices include a safety razor, a piezo-electric crystal, battery and a circuit for coupling the battery to the piezo-electric crystal. These devices are used for removing excess hair from a person's face and do not remove any skin. Such devices are configured for non-professional use.

In addition to manual treatment, cleansing and moisturizing may be accomplished by way of hand-held devices. For example, US Patent Application Publication No. US 2005/0043653 A1 and U.S. Pat. Nos. 5,931,859 and 6,119,035 disclose hand held devices for dispensing a liquid to a person's face. These devices include a cleansing mode in which a micro-current is applied to cleanse the skin. US Patent Application Publication No. US 2008/0139974 A1 discloses a hand held device for just applying a moisturizing liquid to a person's face. An example of such a device is also disclosed in: http://www.voutube.com/watch?v=W1PcSf253cs.

Other hand-held devices are known for cleansing facial skin which rely on ultrasonic frequencies. Examples of these devices are disclosed in Japanese Patent No. JP20000060427; South Korean Patent Nos.: KR 20040022550 and KR 20080006875. Additional examples of such devices can be found at the following locations: http://www.youtube.com/watch?NR=1&v=jypKIrpGDIg&feature=fvwp; http://www.youtube.com/watch?v=fmSS2uexmac and http:/dermasonic.com/how.html. Such devices are also configured for non-professional use.

Dermabrasion is a cosmetic surgical procedure for removing an outer layer of skin by abrading the skin with fine sandpaper or wire brushes to remove scars or other imperfections. This procedure is used to abrade the skin down to the dermis. The dermis is a layer of skin between the epidermis and subcutaneous tissues that consist of connective tissue and cushions the body from stress and strain. Dermabrasion normally requires an anesthetic and is normally done by medical professionals, such as dermatologists. Because of the possibility of infections and scarring, dermabrasion is a relatively unpopular choice for facial skin treatment.

Hand held devices for performing dermabrasion are known. Exemplary hand-held devices used for dermabrasion are disclosed and described in detail in U.S. Pat. No. 8,052,662 and US Patent Application Publication Nos. US 2003/0233085 A1; US 2004/0185067 A1; US 2007/0293795 A1; US 2009/0048557 A1; US 2009/0124985 A1; and US 2013/0144280 A1. In general, such devices include an applicator having an abrasive material applied to the surface. The applicator is attached to a piezo-electric crystal for vibrating the applicator at ultrasonic frequencies. The vibrating applicator is applied to areas of the face of interest. U.S. Pat. No. 7,384,405 discloses a hand-held device that includes a rotating brush with abrasive bristles. Hand-held dermabrasion devices are known to be available for professional and non-professional use.

Debridement is a surgical technique performed by a licensed physician for removing unhealthy tissue, such as. necrotic, i.e., dead, infected, damaged, contaminated tissue or in situations to remove a foreign body in the tissue. US Patent Application Publication No. US 2012/0101512 A1 discloses a hand held device that is known to be used for debridement. The device includes blade carried by a handle. The blade is a small, dull flat blade operable to scrape the necrotic tissue away from the tissue site without harming any of the healthy tissue located adjacent the necrotic tissue. A piezoelectric crystal is attached to the blade to vibrate the blade at ultrasonic frequencies. Such debridement devices are only available for professional use.

Dermaplaning is a relatively popular process that is relatively simple and safe and is used for exfoliating the epidermis, i.e. outer layer of cells in the skin, and removing fine vellus hair, i.e. peach fuzz, from the skin. Dermaplaning is a process normally performed by licensed skin care professionals, such as, estheticians. Using a scalpel and a delicate touch, the scalpel is swept across the skin with light feathering strokes to exfoliate the skin. Exfoliation involves the removal of the oldest dead skin cells on the skin's outermost surface.

Dermaplaning facial skin has many benefits. For example, removing epidermal skin allows skin care products to penetrate more readily into deeper layers of the skin for better results. As mentioned above, dermaplaning removes vellus hair which tends to cause a build-up of dirt and oils in the follicles. Removal of the hair results in healthier looking skin.

Hand-held devices used for dermaplaning normally include a surgical style scalpel consisting of a blade and a handle. Such scalpels are not available for non-professional use. As such, dermaplaning is only available at spas with licensed skin care professionals. Such dermaplaning treatments at spas can be relatively expensive. Unfortunately, there are no known dermaplaning devices known for non-professional home use.

Thus, there is a need to provide a hand-held device and method for dermaplaning for non-professional use that overcomes this problem.

SUMMARY OF THE INVENTION

Briefly, the present invention relates a method and a hand-held device for dermaplaning that is relatively safe for non-professional use. The hand-held device includes a blade with a safety cage forming an assembly removably mounted to a housing. The safety cage limits the depth that the blade can penetrate the skin which makes the device safe for use by non-professionals. Various embodiments of the hand-held dermaplaning device are contemplated. In one embodiment, a piezo-electric crystal is attached to the blade to cause the blade to vibrate at ultrasonic frequencies. A motor driving an eccentric load may also be attached to the blade for vibrating the blade at other frequencies. In one embodiment, the motor and the piezo-electric crystal are selectively and alternatively connectable to the blade. In another embodiment, the device only includes the piezo-electric crystal coupled to the blade. In yet a further embodiment, the device only includes the motor and the eccentric load coupled to the blade. In embodiments that include a motor, the motor speed may be optionally adjustable to enable the vibration frequency to be varied. In accordance with an important aspect of the invention, the blade includes a safety guard for limiting the amount of penetration of the blade into the facial skin to enable the device to be safely used by non-professionals. The invention also includes dermaplaning process that can be used by non-professionals.

DESCRIPTION OF THE DRAWING

These and other advantages of the present invention will be readily understood with reference to the following specification and attached drawing wherein:

FIG. 3 is side elevational view in section of the dermaplaning device illustrated in FIG. 1.

FIGS. 4a-4d is an exemplary schematic of a 4 phase rotary electric switch for use with the present invention, wherein FIG. 4a discloses an OFF position; FIG. 4b illustrates a position in ultrasonic mode; FIG. 4c illustrates an intermediate OFF position and FIG. 4d illustrates a sonic mode.

FIG. 7 is similar to FIG. 1 but without the thumbwheel

FIG. 8 is an exploded view of an alternate embodiment of a dermaplaning device in accordance with the present invention that only includes a piezo-electric crystal.

FIG. 13 is side elevational view in section of the dermaplaning device illustrated in FIG. 12.

FIG. 13a is an alternate embodiment of the device illustrated in FIG. 12 illustrating a removable blade.

FIGS. 13b, 13c and 13d illustrate how the removable blade is attached to the scalpel.

FIG. 13e is a side elevational view illustrating the removable blade attached to the scalpel.

FIG. 13f is similar to FIG. 13e but illustrating the removable blade removed from the scalpel.

FIG. 13g is another alternate embodiment of the of the device illustrated in FIG. 12.

FIG. 16 is a partial side elevational view of the dermaplaning device in accordance with the present invention illustrating the removable blade attached to a handle portion of the housing.

FIG. 16a is an enlarged partial view of the blade illustrating the safety cage and the blade housing.

DETAILED DESCRIPTION

The present invention relates to a method and a hand-held device for dermaplaning that is relatively safe for non-professional use. Various embodiments of the hand-held dermaplaning device are contemplated, as discussed below. The hand-held device includes a blade assembly removably mounted to a housing in one embodiment. In accordance with an important aspect of the invention, the blade includes a safety cage juxtaposed over the cutting edge of the blade for limiting the amount of penetration of the blade into the facial skin to enable the device to be safely used by non-professionals. Another aspect of the invention relates to a dermaplaning process that can be used by non-professionals.

Figure 1:
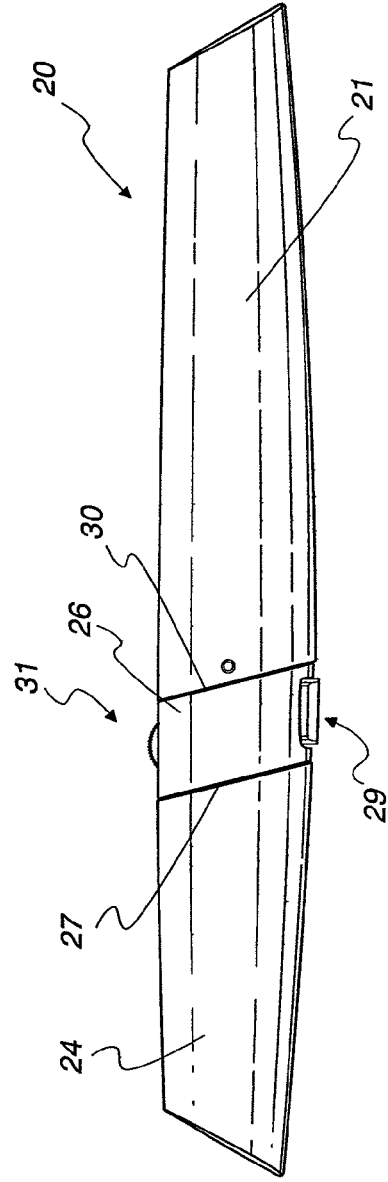
FIG. 1 is a side elevational view of an exemplary dermaplaning device in accordance with the present invention.
Figure 2:
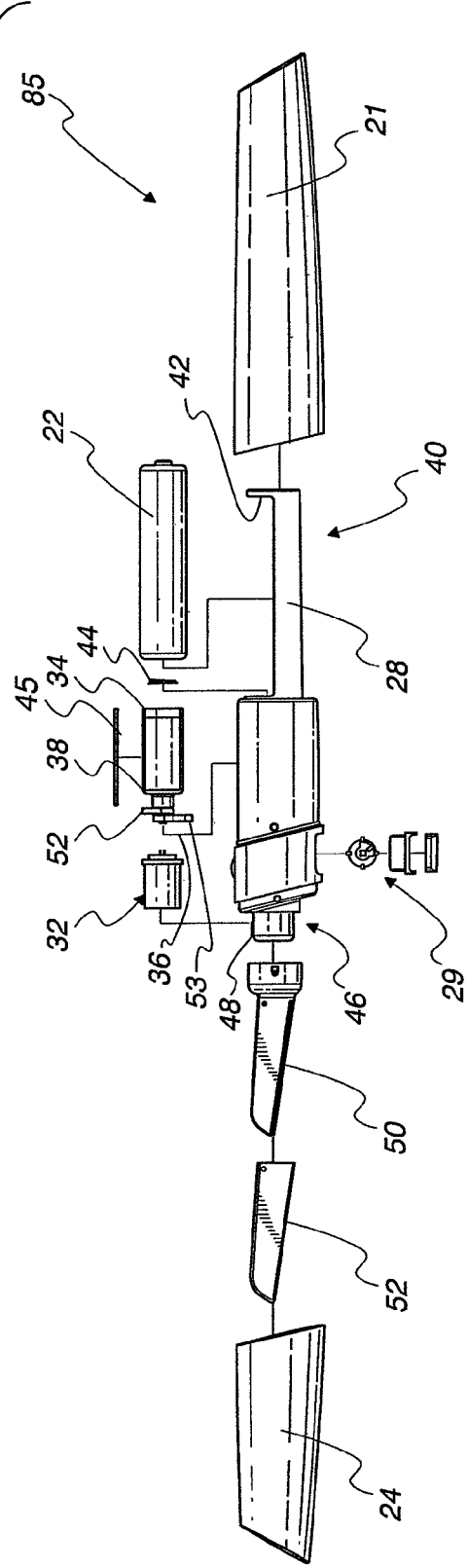
FIG. 2 is an exploded view of one embodiment of the dermaplaning device illustrated in FIG. 1.

Three exemplary embodiments of the dermaplaning device are described and illustrated. All three embodiments include an exemplary outer housing, for example, as illustrated in FIGS. 1 and 7 and a blade assembly complete with a safety cage, and a vibration generator, such as a piezo-electric circuit for generating ultrasonic vibrations or a motor with an eccentric attached to the output shaft, as discussed below. The first embodiment is illustrated in FIGS. 2-6. The first embodiment includes a piezo-electric crystal circuit for vibrating the blade at an ultrasonic frequency, for example, frequencies above 20,000 Hertz and a motor with an eccentric rotary load which vibrates the blade assembly at frequencies other than ultrasonic frequencies, for example, frequencies less than 20,000 Hertz. The second embodiment is illustrated in FIGS. 7-10. In this embodiment, the dermaplaning device only includes a piezoelectric crystal circuit attached to the blade. The third embodiment is illustrated in FIGS. 11-14. In this embodiment, the dermaplaning device includes an outer housing as shown in FIG. 1 and includes a motor with a rotary eccentric load as a vibration generator.

FIGS. 13a-13f illustrate an embodiment with a 2 piece blade assembly which includes a scalpel and a removable blade. In this embodiment, the scalpel may be fixedly mounted to the main housing or alternatively may be coupled to the main housing with a bayonet mount or other conventional coupling means.

Outer Housing

As mentioned above, FIG. 1 illustrates an exemplary outer housing, generally identified with the reference numeral 20 that can be used with the various embodiments that include piezo-electric crystal and circuit and/or a motor and an optional rheostat for controlling the speed of the motor, for example, illustrated in FIGS. 2-6 and FIGS. 12-15. The outer housing 20 may be formed as a cylindrical hollow member closed on each end and formed in two parts by way of injection molded plastic, for example, or other material. Specifically, the outer housing 20 includes an end cap 21 which forms a handle portion and a top cap 24 which forms a cover portion. The cover portion 24 may be configured to attach to a main housing 26, discussed below, at a parting line 27. The handle portion 21 attaches to the main housing 26 at a parting line 30. In this exemplary embodiment, an on-off switch and optional integrated LED (light emitting diode), generally identified with the reference numeral 29, for controlling power to the device is carried by the main housing 26 and may be exposed between the handle portion 21 and the cover portion 24. As discussed in more detail below, an optional thumb wheel control switch 31, carried by the main housing 26, may be used to control the speed of the motor 34.

FIG. 7 illustrates an alternative outer housing, generally identified with the reference numeral 23. The outer housing 23 is used in embodiments that do not include a rheostat and optional thumbwheel.

As used herein, the term housing refers to the outer housing 20 (FIG. 1) and 23 (FIG. 7) individually as well as the combination of the outer housing 21, 23 in combination with the main housing 28 (FIG. 2), individually and collectively.

First Embodiment

Referring first to FIGS. 2-6, a first embodiment of the invention is illustrated and described and identified with the reference numeral 85. The first embodiment of the invention includes a main housing 28, a piezo-electric crystal 32, a DC motor 34, an eccentric rotary load 36, coupled to a shaft 38 and a power supply, such as a battery 22. It is further contemplated that the power supply for the device can be an alternating current power supply. Such alternating current power supplies are well known in the art.

The main housing 28 may be made from an electrically conductive material forming a battery holder portion, generally identified with the reference numeral 40 defining a positive battery contact 42 and a negative battery contact 44. As will be discussed in more detail, below, a portion of the wiring between the various devices can be accomplished by way of a printed circuit board 45 which may be formed from a flexible printed circuit board Alternatively, the printed circuit board 45 may be omitted and the connections between the various devices can be made with electrical wiring.

Figure 17:
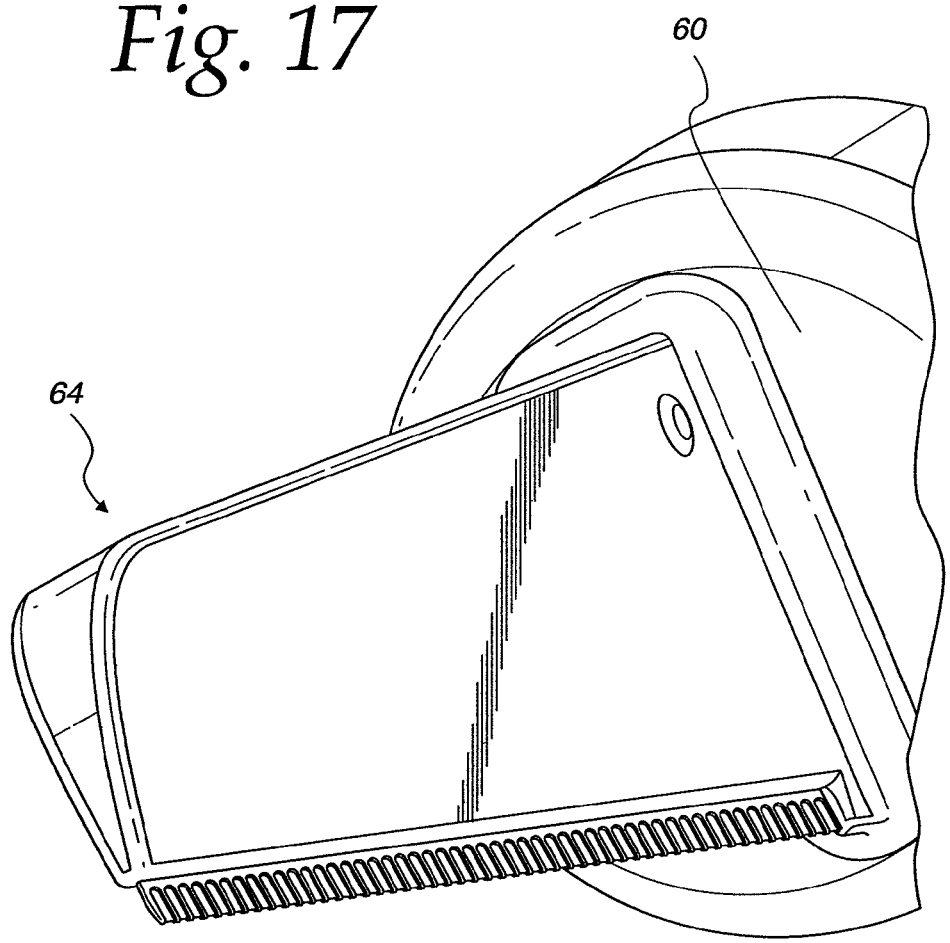
FIG. 17 is a partial isometric view illustrating an exemplary blade guard.

One end 46 of the main housing 28 may be formed with a reduced diameter cylindrical portion 48 which accomplishes several functions. First, as best shown in FIG. 3, an interior portion of the reduced diameter cylindrical portion 48 is configured to provide a friction fit for the piezo-electric crystal 32. Second, as best shown in FIG. 17, the exterior portion of the reduced diameter cylindrical portion 48 provides a bayonet interface for an exemplary replaceable blade 50 mounted with a bayonet interface that cooperates with the bayonet interface on the exterior portion of the reduced diameter portion 48. In accordance with an important aspect of the invention, a safety cage 66 (FIG. 16a) fits over the blade 50 to limit the penetration of the blade 50 into the facial skin.

Turning to FIG. 3, a sectional view of the first embodiment of the dermaplaning device 85, is illustrated. FIG. 3 illustrates the main housing 26 in detail and how all of the various components fit into it. As shown, the various components may be wired and connected, for example, by soldering to the printed circuit board 45.

As mentioned above, this embodiment includes a piezo-electric crystal for vibrating the blade 46 at an ultrasonic frequency defining an ultrasonic mode of operation. The device may also include a DC motor with at least one eccentric rotary loads, generally identified with the reference numeral 51 for generating a vibration frequency other than an ultrasonic vibration frequency defining a sub-ultrasonic frequency mode. The eccentric may be formed as a semi-circular disc 51. A stationary bearing 53 may be disposed axially outwardly from the disc 51 to stabilize the motor shaft 32. Depending on the speed of rotation of the motor shaft, a vibration will be created which will be transmitted to the blade assembly 50.

Driver circuits that drive piezo-electric crystals to generate ultrasonic sound waves/vibrations are well known in the art. Such circuits normally include an alternating current or voltage applied to the piezo-electric crystal. Examples of such driver circuits are disclosed in U.S. Pat. Nos. 3,509,626; 3,967,143 and US Patent Application Publication No. US 2003/0233085 A1. Such a driver circuit is also disclosed in South Korean patent publication no. KR 2004 0022550, all incorporated herein by reference. All references to a piezo electric devices are to be understood to include the driver circuit that causes the piezoelectric device to generate ultrasonic sound waves/vibrations. The driver circuit including its respective components may be disposed on the printed circuit board 45.

Figure 5:
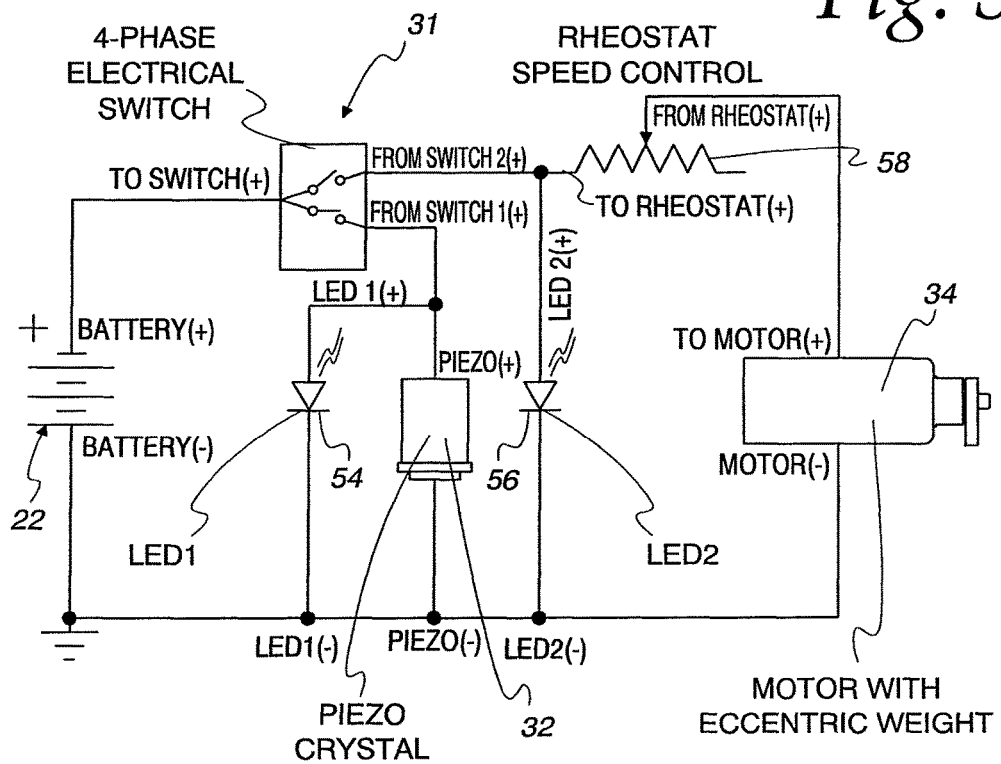
FIG. 5 is an exemplary schematic for the dermaplaning device illustrated in FIG. 3 illustrating an embodiment that includes a piezo-electric crystal, a motor with an eccentric load and an optional rheostat for controlling the speed of the motor.
Figure 6:
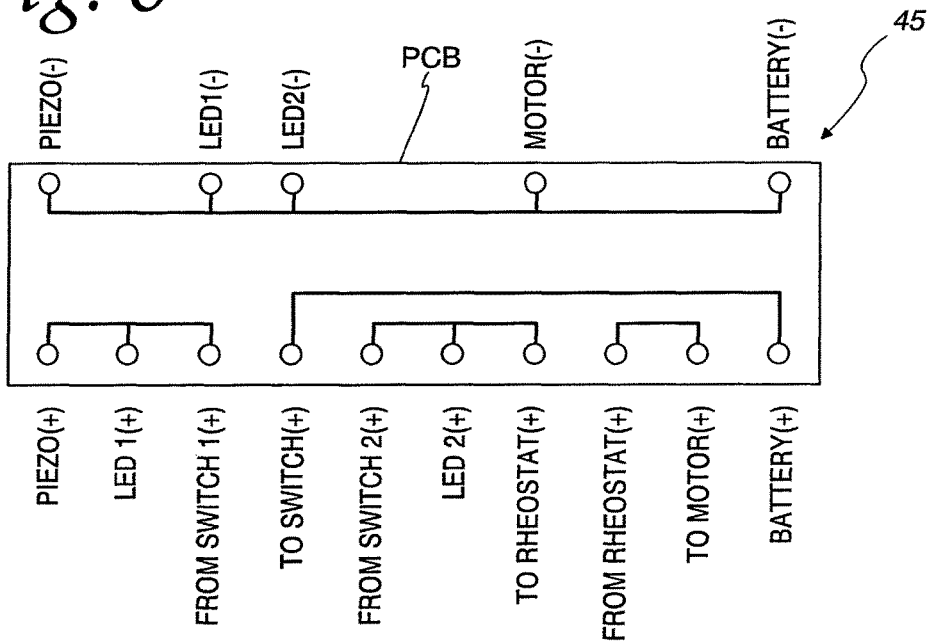
FIG. 6 is a top plan view of an exemplary printed circuit board for use with the embodiment illustrated in FIG. 5.
Figure 9:
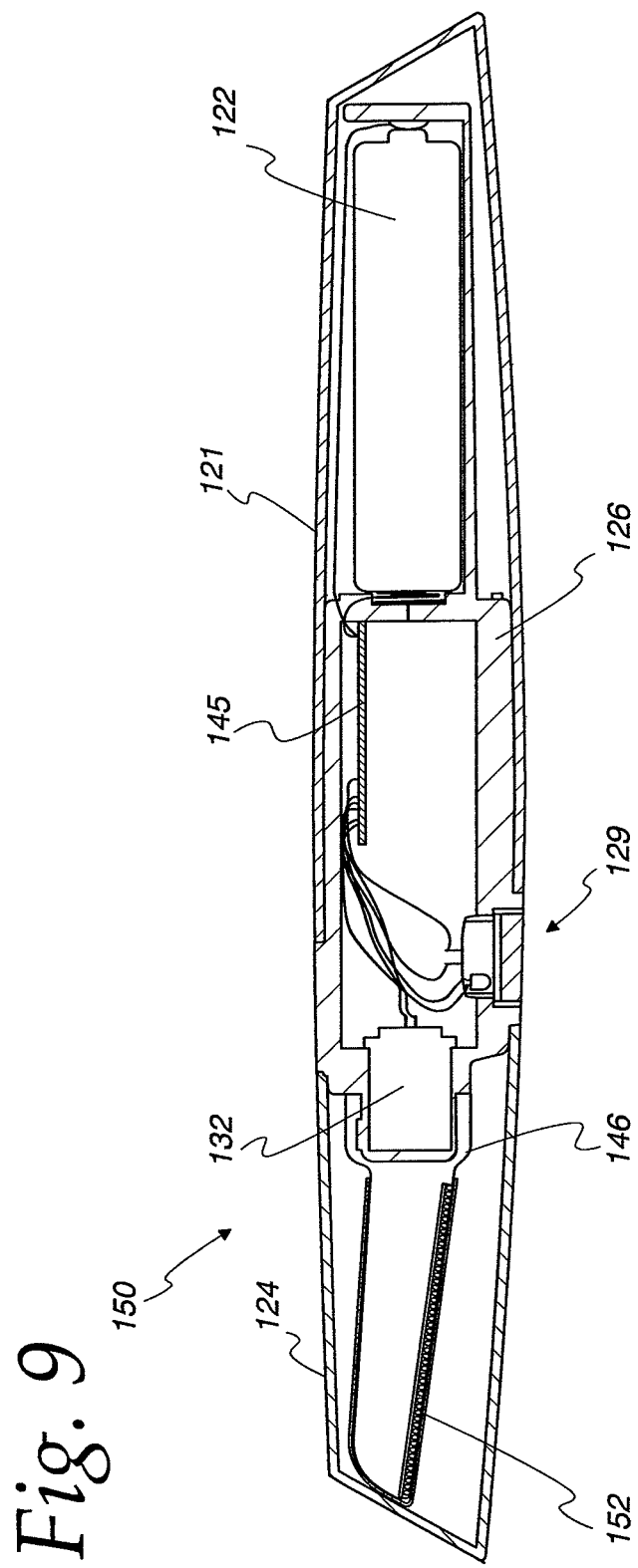
FIG. 9 is side elevational view in section of the dermaplaning device illustrated in FIG. 8

FIGS. 4-6 illustrate the electrical details for controlling a device 50 that includes a piezoelectric element 32 and a DC motor 34 with at least one eccentric rotary load 51. A key aspect of the control is an optional exemplary 4-position rotary switch 31, as illustrated in FIGS. 4a-4d. Such 4 position switches are commonly available and include 4 wires. Normally open rotary contacts are provided between terminals 3 and 4 for controlling power to the piezo-electric crystal 32 and between terminal 1 and 2 for controlling power to the DC motor 34. The terminals 2 and 3 are connected together and to the positive terminal of the battery 22.

In a first position of the rotary switch 31, as shown in FIG. 4a, the contact between terminals 3 and 4 for controlling the power to the piezo-electric crystal 32 is open as is the contact between the terminals 1 and 2 for controlling power to the DC motor 34 is open. As such in the position illustrated in FIG. 4a, no power is delivered to either the piezo-electric crystal 32 or the motor 34. In a second position of the rotary switch 31, as illustrated in FIG. 4b, the contact between the terminals 3 and 4 is closed, thus providing power, i.e. connecting the + battery terminal, to the piezo-electric crystal 32. Since the contact between the terminals 1 and 2 is open, no power is delivered to the motor 34 when the switch 31 is in the position, as illustrated in FIG. 4b. FIG. 4c illustrates another OFF position in which the contact between the terminals 3 and 4 and the contact between the terminals 1 and 2 are both open, thus disconnecting the power from both the piezo-electric crystal 32 and the motor 34. FIG. 4d illustrates a position of the switch 31 in which the contact between the terminals 1 and 2 is closed thus providing power to the motor 34. Since the contact between terminals 3 and 4 is open in this position, no power is delivered to the piezo-electric crystal 32 in this position.

An exemplary schematic diagram for the dermaplaning device 85 is illustrated in FIG. 5. As shown, the circuit is powered by the battery 22. As discussed above, the rotary switch 31 enables the battery 22 to be selectively connected to the piezo-electric crystal 32 or alternatively to motor 34 defining an ultrasonic mode or a sub-ultrasonic frequency mode, respectively. Optional LEDs 54 and 56 may be provided to indicate the mode of the device 50. In particular, the LED 54 is connected in parallel with the piezo-electric crystal 32. Thus, any time the piezo-electric crystal 32 is connected to the positive terminal of the battery 22, the LED 54 is illuminated indicating that the device 50 is operating in an ultrasonic mode of operation. Similarly the optional LED 56 is connected essentially in parallel with the motor 34. Thus, any time the motor 34 is connected to the positive terminal of the battery 22, the LED 56 will be illuminated indicating a sub-ultrasonic mode of operation. Both LEDs 54 and 56 will be off when neither the piezo-electric crystal 32 nor the motor 34 are connected to the positive terminal of the battery 22.

An optional rheostat 58 may be connected in series with the motor 34. As is known in the art, the speed of a DC motor can be control the voltage applied to the motor. The optional rheostat 58 is adjustable and can be controlled to vary its resistance, which, in turn, varies the current and voltage to the motor 34. By varying the speed of the motor 22, the vibration frequency can be varied. As shown in FIG. 1, an optional thumb wheel 31 is accessible from outside the housing 20 to allow the rheostat 58 to be adjusted. The motor 34 may be operated at 600 RPM, for example.

FIG. 6 is an optional and exemplary printed circuit board 45 which may be used to connect the various components to the circuit. It is contemplated that the configuration of the printed circuit board 45 may be different from that shown. Also, various conventional techniques are contemplated for connecting the various components to the printed circuit board 45. One such technique is soldering. Alternatively, the printed circuit board 45 can be omitted and connections between the various components be made with electrical wires. It is also contemplated that the rotary switch 31, as well as the optional LEDs 54 and 56 and the optional rheostat 58 can be mounted on the printed circuit board 45.

Second Embodiment

Figure 10:
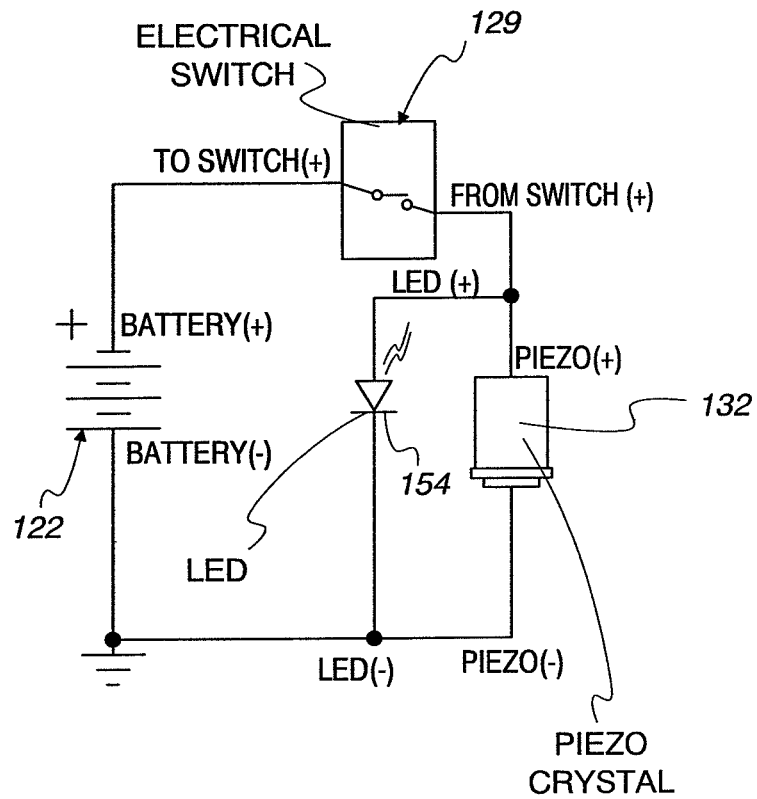
FIG. 10 is an exemplary schematic diagram of the dermaplaning device illustrated in FIG. 8.
Figure 11:
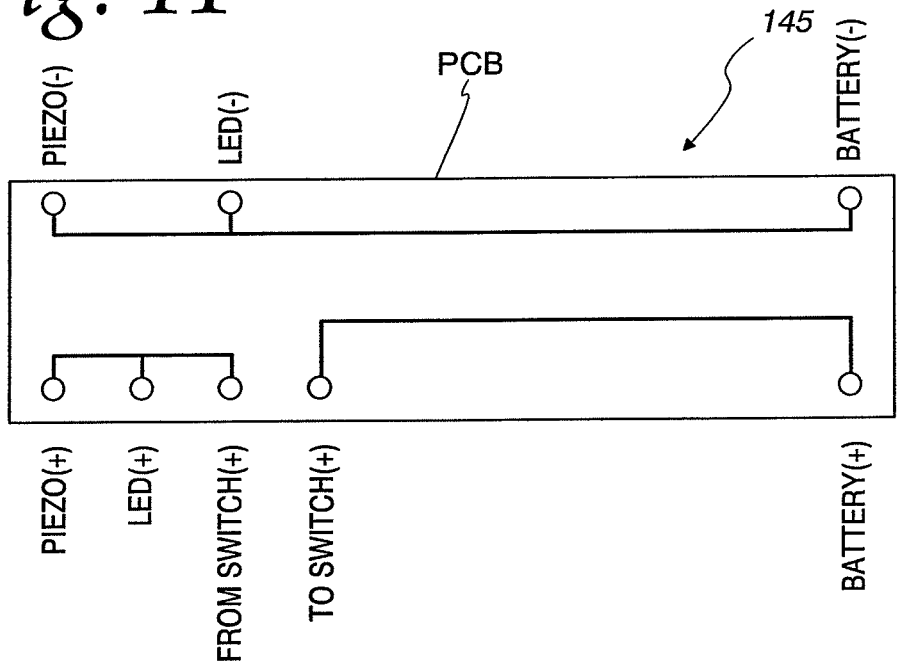
FIG. 11 is an exemplary printed circuit board for use with the dermaplaning device illustrated in FIG. 8.

The second embodiment is illustrated in FIGS. 8-11 and identified with the reference number 185. In this embodiment, like components are identified with like reference numerals with a 1 prefix. In this embodiment, the dermaplaning device 185 only includes a piezoelectric crystal 132. As shown in FIG. 10, a simple single pole single throw micro switch 129 may be used to control the piezo-electric vibration device 132. An optional LED 154 may be included as part of the micro switch 129. A printed circuit board 145 may be provided for making the connections between the various devices. Moreover, the micro switch 129 may be mounted to the printed circuit board 145.

Third Embodiment

Figure 14:
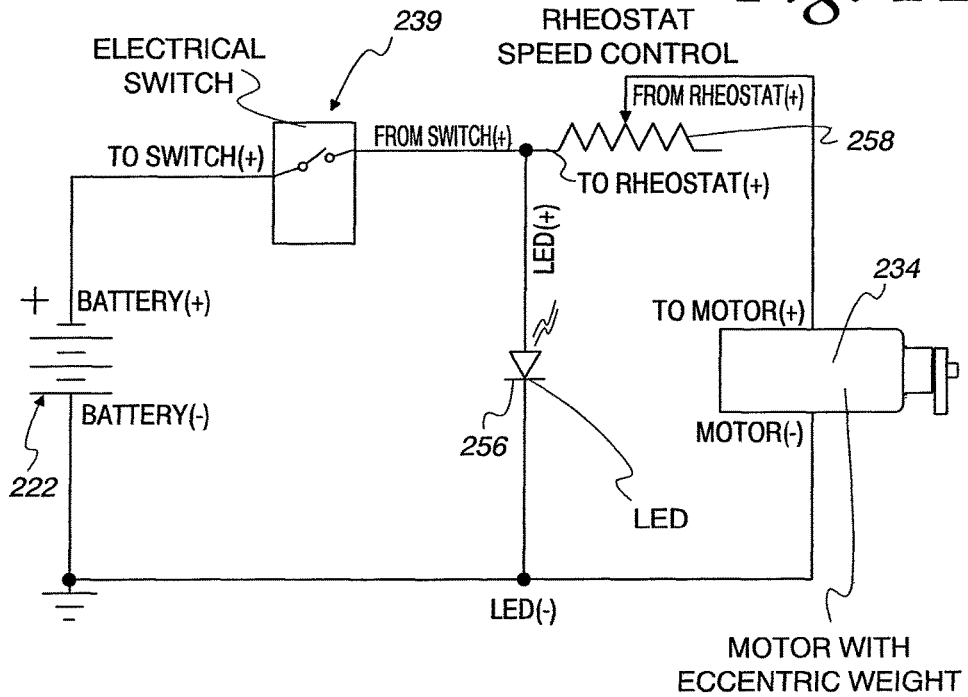
FIG. 14 is an exemplary schematic diagram of the dermaplaning device illustrated in FIG. 12.
Figure 15:
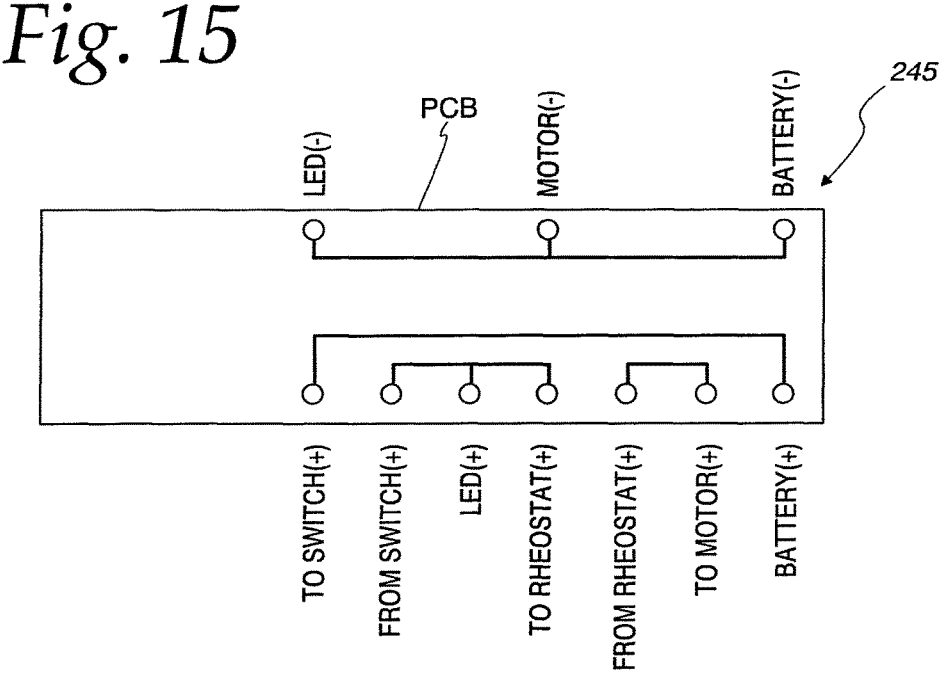
FIG. 15 is an exemplary printed circuit board for use with the dermaplaning device illustrated in FIG. 1.

The third embodiment is illustrated in FIGS. 12-15 and identified with the reference numeral 285. In this embodiment, like components are identified with like reference numerals with a 2 prefix. In this embodiment, the dermaplaning device 285 only includes a motor 234 and the eccentric rotary load 249 supported by a bearing 253. As shown in FIG. 14, a simple single pole single throw micro switch 229 may be used to control power to the motor 234. An optional LED 256 may be included as part of the micro switch 229. In addition, an optional rheostat 258 may be provided for controlling the speed of the motor 234. As shown best in FIG. 13, the rheostat 258 includes a thumb wheel 231. The thumb wheel 231 may optionally be mounted as shown in FIG. 1 to enable adjustment of the motor speed from the outside of the device 250. to A printed circuit board 245 may be provided for making the connections between the various devices. Moreover, the micro switch 229 may be mounted to the printed circuit board 245.

Figure 12:
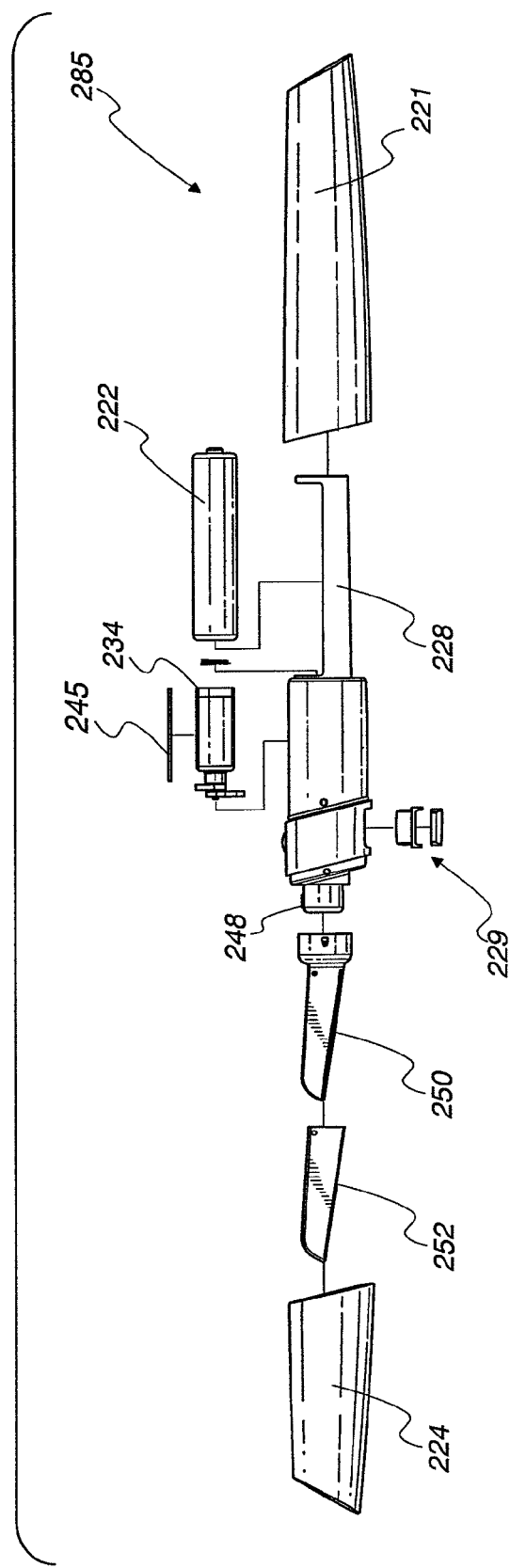
FIG. 12 is an exploded view of another alternate embodiment of a dermaplaning device in accordance with the present invention that only includes a motor and an eccentric load.

An alternate embodiment of the embodiment in FIG. 12 is illustrated in FIG. 13a. In this embodiment, like reference numerals with an "a" suffix are used to identify like parts. In this embodiment no rheostat is provided. Also, in this embodiment as well as the embodiment illustrated in FIGS. 12-15, the printed circuit board may be eliminated. In this embodiment as well as the other embodiments, the blade or scalpel 250a can be bayonet mounted or fixedly mounted to the housing 228a.

In all of such embodiments, the scalpel or blade 250a can be a one piece blade and configured with a bayonet mount, as illustrated and described above. Alternatively, the blade 250a can be formed as a 2 piece device; namely a scalpel 250a with a removable blade 249a, as shown in FIG. 13a. In such an embodiment, the scalpel 250a may be fixedly mounted to the housing 228a. Other configurations of a scalpel with a removable blade are also considered to be within the broad scope of the claims.

Scalpels with removable blades are extremely well known in the art. An example of a scalpel with a removable blade is illustrated and described in detail in U.S. Pat. No. 1,139,796, hereby incorporated by reference. In embodiments with a removable blade 249a, a safety cage 266a, as discussed above, may be formed on the blade 249a. The device illustrated in FIG. 13a may also include a safety cover, for example, a safety cover (not shown) similar to the safety cover 252 as shown in FIG. 12 which fits over the scalpel 250a and the removable blade 249a.

FIG. 13a illustrates the scalpel 250a with a removable blade 249a attached thereto. FIGS. 13b-13d illustrate bow the removable blade 249a is attached to the scalpel 250a. The scalpel 250a is formed with a plurality of posts, for example 3 posts, identified with the reference numerals 253a, 255a and 257a. These posts 253a, 255a and 257a are formed on the scalpel and extend outwardly therefrom on one side as shown. These posts 253a, 255a and 257a are formed to co-operate with slots 259a, 261a and 263a, formed in the removable blade 253a. As shown best in FIG. 13b, the slots 259a and 259b are open slots and are configured to receive the extending posts 255a and 257a on the scalpel 250a. An aperture 263a is formed in the blade 250a for receiving the post 253a formed on the scalpel 250a. As is apparent from FIGS. 13e and 13f, the post 253a is shorter than the posts 255a and 257a. This feature allows the post 253a to snap in place and be received in the aperture 249a and essentially lock the blade 249a in place with respect to the scalpel 250a.

Another alternate embodiment of the embodiment in FIG. 12 is illustrated in FIG. 13g. In this embodiment, like reference numerals with an "b" suffix are used to identify like parts. This embodiment is similar to the embodiment illustrated in FIG. 13a except in this embodiment, the device 285 is provided with a one-piece blade 252b that attaches to the device by way of a bayonet mount, as discussed above. In this embodiment a blade cover 270b is provided. The blade cover 270b may be provided with a c-type cross-section and formed with a spring force causing buttons, generally identified with the reference numeral 272*b* to pinch the blade 252*b* once the cover 270*b* is slid over the blade 252*b*.

The Blade

Figure 18:
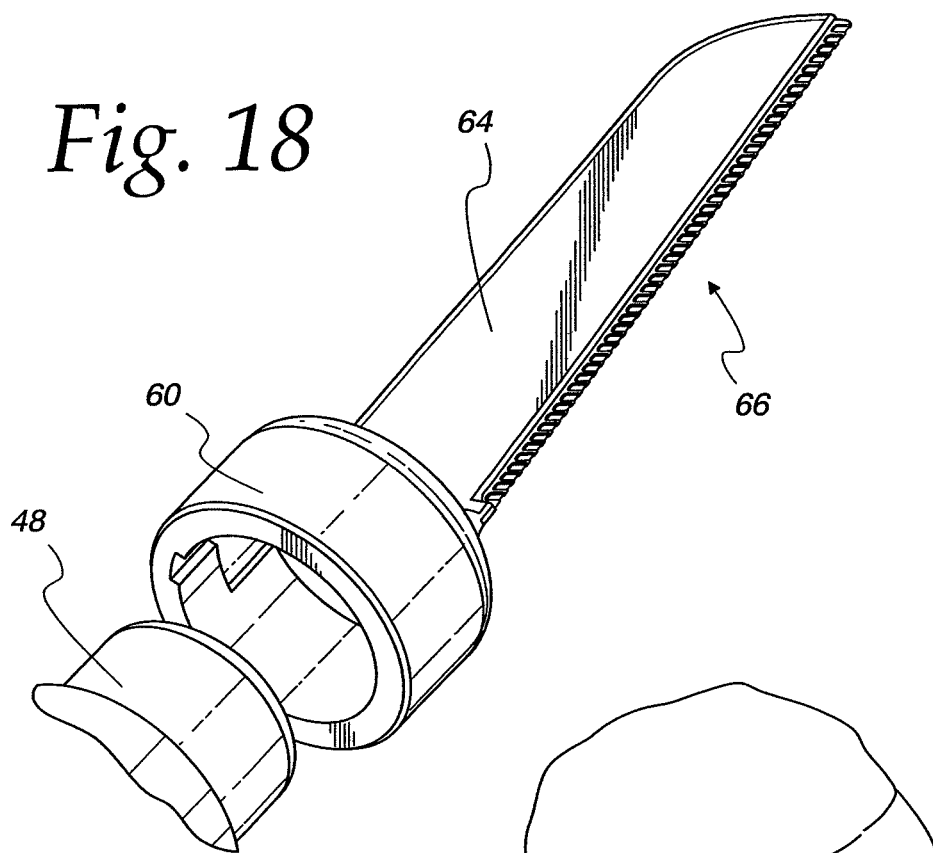
FIG. 18 is a partial isometric view of an exemplary blade for use with the present invention shown removed from the handle portion of the housing illustrating an exemplary bayonet type interface.

An important aspect of the invention relates to the blade assembly 50, 150, 250. The blade assembly 50, 150, 250 is best shown in FIGS. 16-18. As best shown in FIG. 18, the blade assembly 50, 150, 250 is mounted to a generally cylindrical portion 60 and is configured to mate with the cylindrical portion 48 (FIG. 2) attached to the handle portion 21 (FIG. 1). The blade assembly 50. 150, 250 is only used on a single patient. As such, the blade 62 assembly 50, 150, 250 is removable for disposal and replaced for each new client.

As shown in FIGS. 16 and 18, the cylindrical portion 60 of the blade assembly 50. 150, 250 is configured to attach to the cylindrical portion 48 attached to the handle portion 21, for example by way of a bayonet connection. Other connections are also suitable.

In accordance with an important aspect of the invention, the blade assembly 50, 150, 250 includes a surgical blade or scalpel 62 and a molded housing 64, shown best in FIG. 17 with a wedge shaped cross section. The blade 62 extends along an axis generally parallel to or at an acute angle with respect to a longitudinal axis of the device housing 20 (FIG. 1), 23 (FIG. 7).

In order to limit the depth of the cut into the skin and to prevent non-professionals from accidentally cutting below the epidermis layer of facial skin, a safety cage 66 is juxtaposed over an extending portion of the blade 62. More particularly, the safety cage 66 extends over a cutting edge 67 of the blade 62 and extends from the blade housing 64. As best shown in FIG. 16*a*, the safety cage 66 is formed as an exemplary comb-like structure defining posts 68 and valleys 70. The comb-like structure 66 may be injection molded over the cutting edge 67 of the blade 62. Alternatively, the comb-like structure 66 may be snapped in place over the cutting edge 67 of the blade 62. The depth of the valleys 70 limits the depth of the cut by limiting the depth of the valleys 70, for example, to several millimeters. As such, the blade assembly 50, 150, 250 is rendered safe for use by non-professionals as apart of a dermaplaning device.

As mentioned above, two piece blades or scalpels may be used. In such embodiments, the safety cage is provided over the cutting edge portion of the removable blade.

Process

A process for treating facial skin is described for non-professionals. An exemplary process for treating facial skin by the non-professional is discussed below which includes dermaplaning.
1. Cleanse: This step prepares the skin for the dermaplaning procedure. It effectively removes makeup as well as product residue, while ridding the skin of surface oils. Moisten face with warm water, apply a small amount of cleanser to moist palm, form lather with hands and massage onto face. Rinse with warm water and repeat. Blot skin dry
2. Dermaplane: Use a hand-held dermaplaning device which includes a blade and embedded vibration technology, for example, as disclosed above, that is safe for use by non-professionals which safely exfoliates the skin. Dermaplaning devices with a blade and embedded vibration technology other than the one described herein are also suitable. The vibration technology maximizes the blades efficiency while stimulating micro circulation and lymphatic activity. Skin is not only deeply exfoliated, but all traces of built up debris and vellus hair are removed. Skin is left baby soft, product penetration is maximized.

Figure 19:
FIG. 19 illustrates a partial isometric view of a person using the dermaplaning device in accordance with the present invention.
Figure 20:
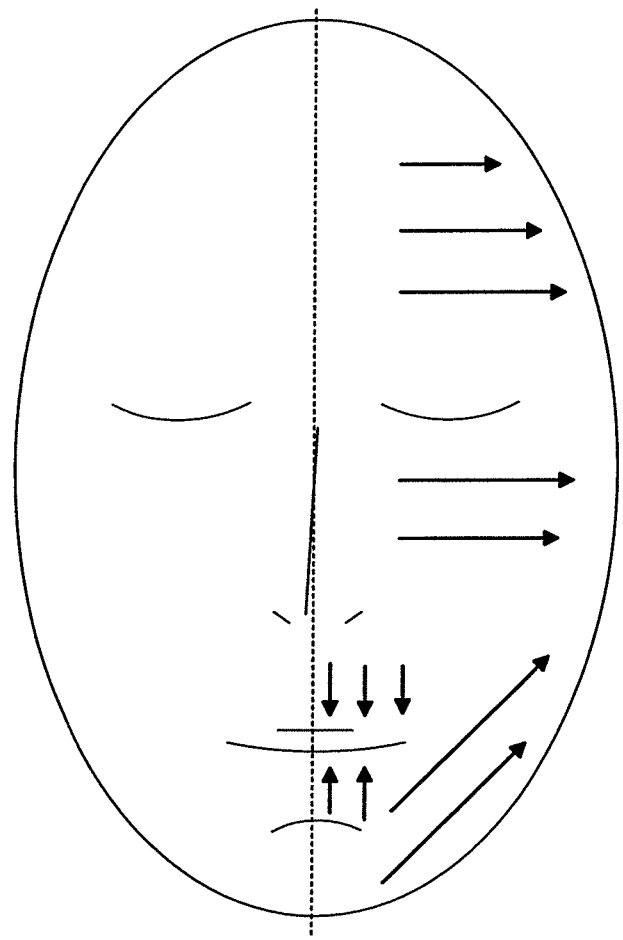
FIG. 20 is drawing of a face with the arrows illustrating the direction of the strokes of the dermaplaning device on a user's face.

Begin by grasping the and switching on the device. A subtle vibration will immediately be noticed.
As illustrated in FIGS. 19 and 20, begin the treatment at the center of face focusing on right side, using gentle yet firm pressure move the device across forehead and towards hair line, following the contours of your face, avoiding the brow and eye area.
Once you have completed the upper face move to the lower face and begin again at the centerline using the same gentle but firm pressure moving the device along the jawline up toward the ear. Continue working up and onto the cheek moving from the nose toward the ear following the contour of the cheek. The nose and eye area should be avoided. When working around the mouth use short strokes with gentle yet firm pressure and move toward the vermillion border (edge of lip) and avoid the surface of the lip.
The dermaplaning device is very efficient at exfoliating the skin and no more than two passes in any area are necessary. When the right side of the face is completed, move to the left side, following the same pattern.
3. Peel:
A chemical peel completes the exfoliation process. Various chemical peels are suitable. For example, a chemical peel comprising a blend of alpha and beta hydroxy acids combined with an anti-oxidant compound, for example, Bioperfect's Anti-Oxidant Complex, completes the exfoliation process and amplifies cellular turnover to help stimulate production of collagen. This peel is to be used immediately following the use of the dermaplaning device.
Open prepared peel pad. Begin on forehead, apply peel to entire face and neck beginning on forehead and using a circular motion. Avoid contact with delicate eye and lip areas.
4. Post Treatment Comforting Balm—Use a balm that has been specifically formulated to comfort, nourish, and protect delicate post treatment skin. The balm is absorbed deeply into newly exfoliated skin, leading to optimum absorption of our proprietary multi-dimensional complex of cosmeceuticals.
Use a small amount and massage into face and neck avoiding eye area.

Obviously, many modifications and variations of the present invention are possible in light of the above teachings. For example, one or more of the steps in the process excluding the dermaplaning step may be eliminated. Thus, it is to be understood that within the scope of the appended claims, the invention may be practiced otherwise than as specifically described above.

What is claimed and desired to be secured by a Letters Patent of the United States is:

1. A portable hand-held dermaplaning device comprising:
a housing for carrying respective components, wherein said respective components comprise:
a blade assembly having a blade and a safety cage, the safety cage being attached to the blade and the blade configured to remain stationary relative to said safety cage during use of the dermaplaning device, said blade assembly removably mounted with respect to said housing, said blade assembly carried by said housing to enable said blade to penetrate an epidermis during use, said safety cage juxtaposed over said blade and constructed and arranged to limit the depth of cut from cutting below the epidermis wherein portions of said safety cage extend below a cutting edge of said blade;

a vibration generator mechanically coupled to said blade assembly for selectively generating vibrations to vibrate said blade assembly at a predetermined frequency;

a power supply for powering the vibration generator;

a switch for selectively connecting said power supply relative to said vibration generator in an on mode of operation, wherein the blade remains stationary relative to the safety cage, and disconnecting said power supply from said vibration generator in an off mode of operation; and wherein said housing is formed to carry said blade assembly, said vibration generator, said power supply, and said switch.

2. The portable hand-held dermaplaning device as recited in claim 1, wherein said vibration generator includes a piezo-electric crystal.

3. The hand-held dermaplaning device as recited in claim 1, wherein said vibration generator includes a motor and an eccentric rotary load.

4. The hand-held dermaplaning device as recited in claim 1, wherein said vibration generator includes a piezo-electric crystal and a motor and said switch is configured to enable one or the other piezo-electric crystal and said motor to he alternatively selected.

5. The hand-held dermaplaning device as recited in claim 1, wherein said blade extends along an axis generally parallel to a longitudinal axis of said main housing.

6. The portable hand-held dermaplaning device as recited in claim 1, wherein said housing includes a handle portion.

7. The portable hand-held dermaplaning device as recited in claim 1, wherein said blade is a surgical blade.

8. The hand-held dermaplaning device as recited in claim 1, wherein said power supply includes a battery.

9. The hand-held dermaplaning device as recited in claim 1, wherein said power supply is an alternating current power supply.

10. The hand-held dermaplaning device as recited in claim 1, further including a printed circuit board for connecting said switch, said power supply and said vibration generator together.

11. The hand-held dermaplaning device as recited in claim 1, wherein said safety cage is snapped in place over the cutting edge of the blade.

12. The hand-held dermaplaning device as recited in claim 1, wherein said safety cage is formed as a comb-like structure.

13. The hand-held dermaplaning device as recited in claim 1, wherein said safety cage is injection molded over the cutting edge of the blade.

14. The hand-held dermaplaning device as recited in claim 1, further comprising an LED constructed and configured to illuminate when the dermaplaning device is in use.

* * * * *